United States Patent
Augustine et al.

(10) Patent No.: US 6,987,209 B2
(45) Date of Patent: Jan. 17, 2006

(54) FLEXIBLE NON-CONTACT WOUND TREATMENT DEVICE

(75) Inventors: Scott D. Augustine, Bloomington, MN (US); Randall C. Arnold, Minnetonka, MN (US); Gregory P. Hamlin, St. Paul, MN (US); Donald E. Stapf, Minneapolis, MN (US); Keith J. Leland, Minnetonka, MN (US)

(73) Assignee: Arizant Healthcare Inc., Eden Prairie, MN (US)

(*) Notice: Subject to any disclaimer, the term of this patent is extended or adjusted under 35 U.S.C. 154(b) by 290 days.

(21) Appl. No.: 10/291,303

(22) Filed: Nov. 8, 2002

(65) Prior Publication Data

US 2003/0069529 A1 Apr. 10, 2003

Related U.S. Application Data

(63) Continuation of application No. 09/547,354, filed on Apr. 11, 2000, now Pat. No. 6,580,012, which is a continuation of application No. 08/838,618, filed on Apr. 11, 1997, now Pat. No. 6,093,160, which is a continuation-in-part of application No. 08/342,741, filed on Nov. 21, 1994, now Pat. No. 5,817,145.

(51) Int. Cl.
  *A61F 13/00* (2006.01)

(52) U.S. Cl. .............. 602/42; 602/2; 602/46; 602/54; 607/96; 607/108; 607/112

(58) Field of Classification Search ........... 602/2, 602/41–59; 128/888, 889; 607/96, 108, 109, 607/112, 113–115
See application file for complete search history.

(56) References Cited

U.S. PATENT DOCUMENTS

| | | |
|---|---|---|
| 222,690 A | 12/1879 | Goldschmidt |
| 697,637 A | 4/1902 | Lee |
| 720,812 A | 2/1903 | Johnson |
| 1,384,467 A | 7/1921 | Homan |
| 1,399,095 A | 12/1921 | Webb, Sr. |
| 1,777,982 A | 10/1930 | Popp |

(Continued)

FOREIGN PATENT DOCUMENTS

| | | |
|---|---|---|
| DE | 31 02 674 | 9/1982 |
| DE | 35 39 533 | 5/1987 |
| DE | G 8305 103.1 | 4/1988 |
| EP | 0355 186 | 2/1990 |
| EP | 0 424 165 | 4/1991 |
| EP | 0 485 657 | 5/1992 |
| EP | 0 607 472 | 7/1994 |
| FR | 1 527 887 | 6/1968 |
| GB | 288 220 | 7/1927 |
| GB | 2 082 919 | 3/1982 |
| GB | 2 199 501 | 7/1988 |
| GB | 2 261 822 | 6/1993 |
| GB | 3090 | 6/2002 |
| WO | 98 46179 | 10/1988 |
| WO | 89 04158 | 5/1989 |
| WO | 94 00090 | 1/1994 |
| WO | 96 15745 | 5/1996 |

*Primary Examiner*—Kim M. Lewis
(74) *Attorney, Agent, or Firm*—INCAPLAW; Terrance A. Meador

(57) ABSTRACT

A non-contact wound treatment device suitable for releasable attachment to a patient's skin surface over a selected wound area in a non-contact position relative to the selected wound area, the wound treatment device comprising an attachment portion suitable for releasable attachment with the patient's skin surface, having an inner perimeter for defining the selected wound area, a wound treatment portion with a substantially planar wound cover and a support member supporting the wound cover, and a transition portion with a membrane connecting the wound treatment portion to the attachment portion, the membrane extending around the outer perimeter of the support member and attached to the attachment portion between the inner and outer perimeter of the attachment portion.

71 Claims, 12 Drawing Sheets

U.S. PATENT DOCUMENTS

| | | | |
|---|---|---|---|
| 1,920,808 A | 8/1933 | Sander | |
| 1,979,082 A | 10/1934 | Schwedenberg et al. | |
| 2,221,758 A | 11/1940 | Elmquist | |
| 2,443,481 A | 6/1948 | Sene | |
| 2,573,791 A | 11/1951 | Howells | |
| 2,577,945 A | 12/1951 | Atherton | |
| 2,599,523 A | 6/1952 | Dorr | |
| 2,601,189 A | 6/1952 | Wales, Jr. | |
| 2,632,443 A | 3/1953 | Lesher | |
| 2,706,988 A | 4/1955 | Weber | |
| 2,769,892 A | 11/1956 | Collins | |
| 3,026,874 A | 3/1962 | Stevens | |
| 3,528,416 A | 9/1970 | Chamberlain | |
| 3,596,657 A | 8/1971 | Eidus | |
| 3,610,238 A | 10/1971 | Rich, Jr. | |
| 3,610,251 A | 10/1971 | Sanderson | |
| 3,687,143 A | 8/1972 | Schneeberger et al. | |
| 3,691,646 A | 9/1972 | Ruffolo | |
| 3,782,377 A | 1/1974 | Rychlik | |
| 3,814,095 A | 6/1974 | Lubens | |
| 3,867,939 A | 2/1975 | Moore | |
| 3,881,477 A | 5/1975 | Von Otto | |
| 4,080,971 A | 3/1978 | Leeper | |
| 4,134,399 A | 1/1979 | Halderson | |
| 4,172,495 A | 10/1979 | Zebuhr et al. | |
| 4,279,255 A | 7/1981 | Hoffman | |
| 4,341,209 A | 7/1982 | Schaar | |
| 4,382,441 A | 5/1983 | Svedman | |
| 4,399,816 A | 8/1983 | Spangler | |
| 4,468,227 A | 8/1984 | Jensen | |
| 4,484,574 A | 11/1984 | DeRusha et al. | |
| 4,517,972 A | 5/1985 | Finch, Jr. | |
| 4,540,412 A | 9/1985 | Van Overloop | |
| 4,572,188 A | 2/1986 | Augustine et al. | |
| 4,628,930 A | 12/1986 | Williams | |
| 4,633,863 A | 1/1987 | Filips et al. | |
| 4,641,641 A | 2/1987 | Strock | |
| 4,641,643 A | 2/1987 | Greer | |
| 4,667,666 A | 5/1987 | Fryslie | |
| 4,890,608 A | 1/1990 | Steer | |
| 4,962,761 A | 10/1990 | Golden | |
| 4,969,881 A | 11/1990 | Viesturs | |
| 5,003,971 A | 4/1991 | Buckley | |
| 5,025,777 A | 6/1991 | Hardwick | |
| 5,060,662 A | 10/1991 | Farnswoth, III | |
| 5,086,763 A | 2/1992 | Hathman | |
| 5,107,832 A | 4/1992 | Guibert et al. | |
| 5,135,518 A | 8/1992 | Vera | |
| 5,144,113 A | 9/1992 | Hall et al. | |
| 5,144,958 A | 9/1992 | Krueger et al. | |
| 5,170,781 A | 12/1992 | Loomis | |
| 5,190,031 A | 3/1993 | Guibert et al. | |
| 5,230,350 A | 7/1993 | Fentress | |
| 5,431,622 A | 7/1995 | Pyrozyk et al. | |
| 5,531,670 A | 7/1996 | Westby et al. | |
| 5,580,346 A | 12/1996 | Spier | |
| 5,609,619 A | 3/1997 | Pompei | |
| 5,817,145 A | * 10/1998 | Augustine et al. | 607/96 |
| 5,947,914 A | * 9/1999 | Augustine | 602/2 |
| 5,954,680 A | * 9/1999 | Augustine | 602/42 |
| 5,964,723 A | * 10/1999 | Augustine | 602/42 |
| 5,986,163 A | * 11/1999 | Augustine | 602/42 |
| 6,093,160 A | 7/2000 | Augustine | |
| 6,110,197 A | * 8/2000 | Augustine et al. | 607/108 |
| 6,267,740 B1 | * 7/2001 | Augustine et al. | 602/2 |
| 6,580,012 B1 | * 6/2003 | Augustine et al. | 602/42 |

* cited by examiner

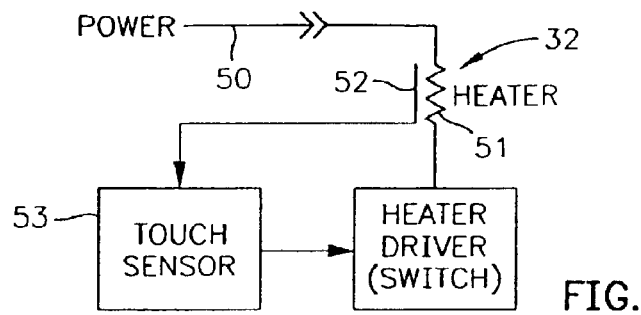
FIG. 8
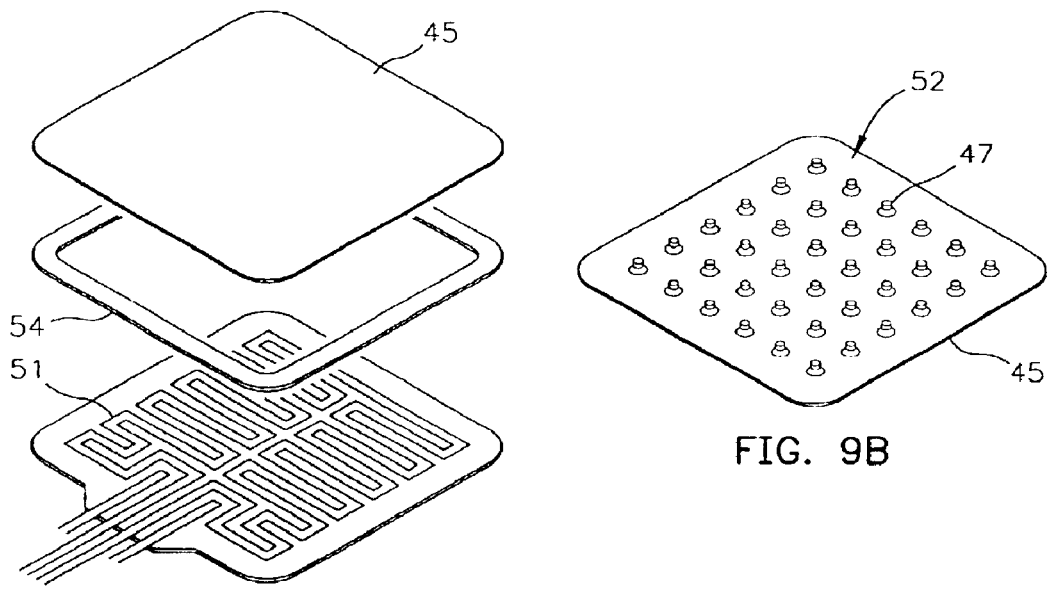
FIG. 9A
FIG. 9B
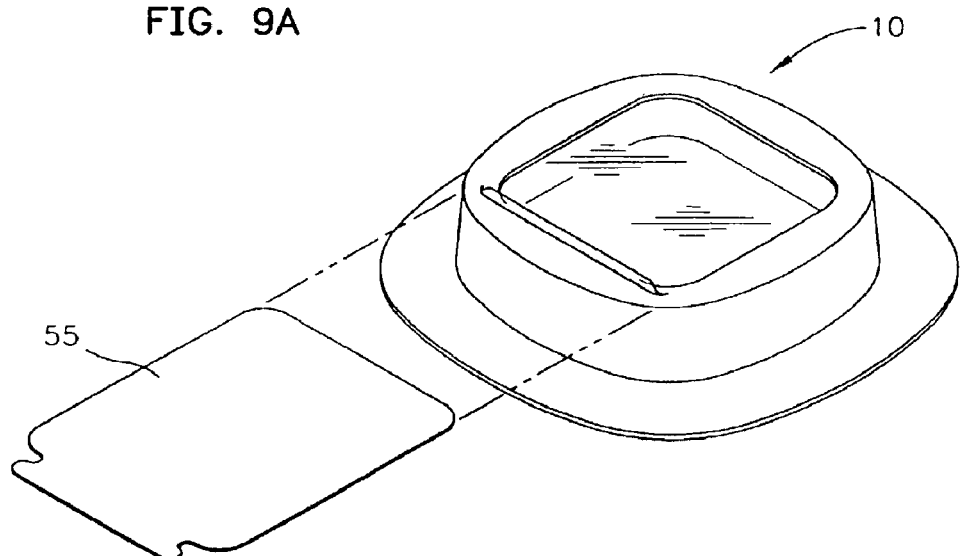
FIG. 10

FLEXIBLE NON-CONTACT WOUND TREATMENT DEVICE

CROSS REFERENCE TO RELATED CASES

This application is a continuation of U.S. patent application Ser. No. 09/547,354, filed Apr. 11, 2000 now U.S. Pat. No. 6,580,012, titled FLEXIBLE NON-CONTACT WOUND TREATMENT DEVICE, which is a continuation of U.S. patent application Ser. No. 08/838,618, filed Apr. 11, 1997, now U.S. Pat. No. 6,093,160, titled FLEXIBLE NON-CONTACT WOUND TREATMENT DEVICE, which is a Continuation-in-Part of U.S. patent application Ser. No. 08/342,741, filed Nov. 21, 1994, now U.S. Pat. No. 5,817,145, titled WOUND TREATMENT DEVICE and having common assignee.

This application contains material related to the following U.S. patents and pending U.S. applications and all assigned commonly with this application:

Ser. No. 07/900,656, filed Jun. 19, 1992 for THERMAL BODY TREATMENT AND APPARATUS, now abandoned;

Ser. No. 08/356,325, filed Feb. 21, 1995 for WOUND COVERING, now abandoned;

Ser. No. 08/785,794, filed Jan. 21, 1997 for NORMOTHERMIC HEATER WOUND COVERING now U.S. Pat. No. 5,986,163;

Ser. No. 08/786,713, filed Jan. 21, 1997 for NORMOTHERMIC TISSUE HEATING WOUND COVERING, now U.S. Pat. No. 5,964,723;

Ser. No. 08/786,714, filed Jan. 21, 1997 for NEAR HYPOTHERMIC HEATER WOUND COVERING, now U.S. Pat. No. 5,954,680;

Ser. No. 08/843,072, filed Apr. 11, 1997 for FLEXIBLE NON-CONTACT WOUND TREATMENT DEVICE WITH A SINGLE JOINT; and Ser. No. 08/999,353, filed Dec. 29, 1997 for WOUND COVERING, now U.S. Pat. No. 5,947,914.

TECHNICAL FIELD

This invention relates to a wound treatment device and, in particular, to a wound treatment device having a substantial portion of a wound cover that is in non-contact with a wound and capable of delivering heat to the wound. More particularly, the wound treatment device includes a flexion joint that maximizes the ability of the wound treatment device to adapt to the contours and movements of a human body.

BACKGROUND OF THE INVENTION

A novel mode of wound treatment is disclosed in detail in published PCT Applications WO 94/00090 and WO 96/15745, both owned in common with this application. This new treatment employs a non-contact wound treatment device that covers a wound, forming a treatment volume about and over the wound. An embodiment of such a wound treatment device may be characterized in having a plurality of parts, three of which are useful for the purpose of description. These three parts are an attachment portion, a wound treatment portion, and a transition portion. Each portion serves a respective function.

The attachment portion connects and retains the wound treatment device on the skin of a person. The wound treatment portion typically includes a standoff that rises above the person's skin surface, and a wound cover that spans an open portion of the standoff. Together, the standoff and wound cover define a wound treatment volume and a wound treatment area onto which the wound treatment volume is projected.

The transition portion connects the attachment portion to the wound treatment portion. An important function of the transition portion is to adapt the wound treatment device to the contour of the portion of a person's body where the device is mounted and to movements of the person's body that deform the wound treatment device in situ. In this regard, an important function of the transition portion is the accommodation of patient motion by the compliance of the transition portion.

Achievement of this important function of the transition portion is challenged by the need to maintain the orientation of the wound cover in the wound treatment portion—both in aspect and location—with respect to the wound being treated. The orientation of the wound cover is difficult to maintain when the wound treatment device is mounted on a highly curved part of a body. While the wound treatment devices disclosed in the referenced PCT applications exhibit excellent adaptability in a surface that is parallel to the surface of the body portion where the wound treatment device is mounted, there is impairment of adaptability and disturbance of the orientation of the wound cover due to limited flexibility in the direction of a Z axis that is perpendicular to the surfaces. If the transition portion is substantially perpendicular to the attachment portion, it may buckle in response to body motion or contour and collapse the standoff in the wound treatment portion. The collapse of the standoff of course alters the orientation of the wound cover with respect to the wound, possibly reducing the effectiveness of the wound treatment device.

Z axis conformability is especially important for a wound treatment device used on a portion of a person's lower leg. The lower leg has a very tight radius of curvature. Therefore, when a three-dimensional wound treatment device is curved around a lower leg, substantial stress results that may result in deformation of the shape of the wound treatment device, in some cases even causing the wound cover to contact the wound.

SUMMARY OF THE INVENTION

The overall flexibility of a wound treatment device is enhanced by an invention based upon the inventors' critical realization that provision of a membrane in the transition portion that connects the wound treatment portion to the attachment portion accommodates patient motion and contour by paying out stored material to flex the wound treatment device in all dimensions of the volume that the wound treatment device occupies.

In this invention, the membrane connects the wound treatment portion to the attachment portion, extending between the wound cover and the attachment portion, around the outside of an outer periphery of the standoff in the wound treatment portion. Under the standoff, the membrane attaches to the attachment portion between inner and outer peripheries of the attachment portion.

Preferably, the inner periphery of the attachment portion along which the membrane is attached is limited to being contained within the outer periphery of the standoff. This permits reduction of the size of the attachment portion, minimizing the total "foot print" of the wound treatment device. A smaller footprint is generally considered to be advantageous particularly when attaching the wound treatment device to a highly curved part of a person's body, such as the surface of a lower leg.

The membrane, its connection of the wound treatment portion with the attachment portion, and its attachment to the attachment portion along an inner periphery of the attachment portion provide a flexion joint, or a double hinge that maximizes the adaptability of the wound treatment device and maintains the orientation of the wound cover over greater ranges of body curvature and movement than previously obtainable.

It is, accordingly, an objective of this invention to provide a flexible, non-contact wound treatment device that adapts to body curvature and motion.

Another objective is the provision of a non-contact wound treatment device having a wound treatment portion, an attachment portion, and a transition portion with a membrane connecting the wound treatment and attachment portions.

It is a related objective in this latter regard to provide a flexion joint between the wound treatment and attachment portions in the form of a membrane in the transition portion.

A significant advantage of the invention is the potential reduction in size of the attachment portion, providing a smaller footprint of the wound treatment device.

BRIEF DESCRIPTION OF THE DRAWINGS

The various figures of the drawing depict illustrative and exemplary forms of the wound treatment device. Throughout the several views, identical reference characters represent similar or equivalent structures wherein:

FIG. 8 is an electrical schematic of a pressure sensitive switch for a heater system;

FIG. 9A is an exploded view of a pressure sensitive switch incorporated into a wound treatment device;

FIG. 9B is a view of a portion of the pressure sensitive switch;

FIG. 10 is a perspective view of a passive heater embodiment of the wound treatment device;

DETAILED DESCRIPTION

Figure 1:
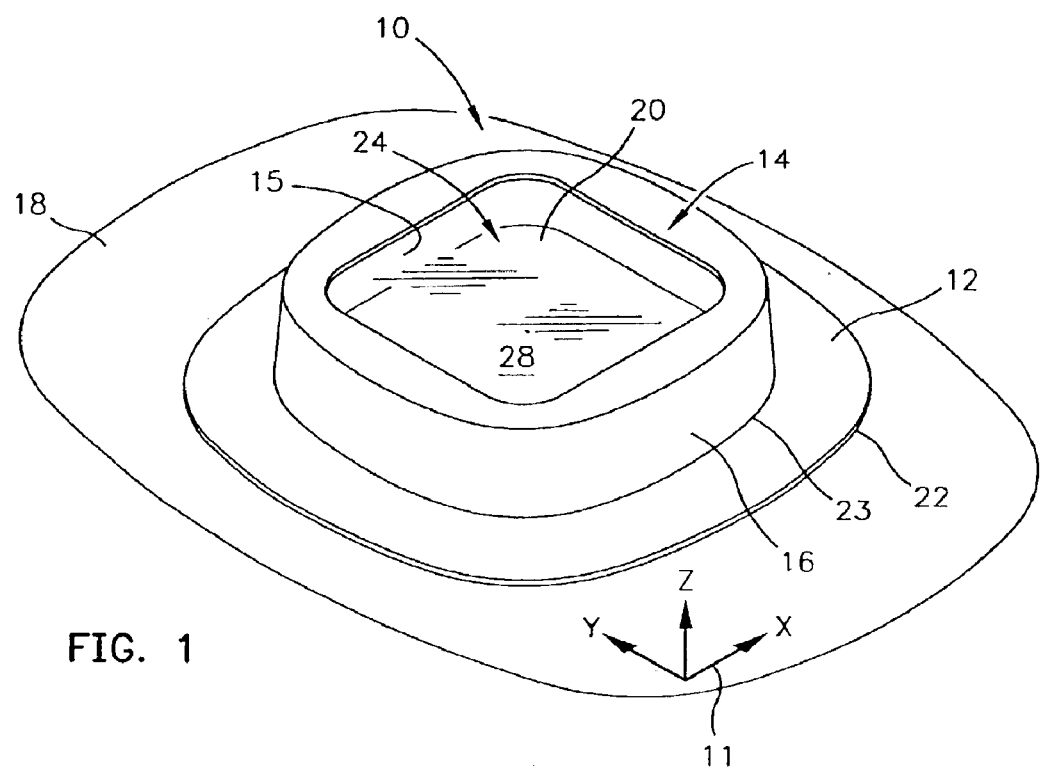
FIG. 1 is a perspective view of one embodiment of the wound treatment device.

For an understanding of the invention that is disclosed and claimed in this application, reference is made to FIGS. 1–10 in which embodiments and elements of a wound treatment device are illustrated. With reference especially to FIG. 1, a wound treatment device 10 has a planar upper surface displaced above the skin surface of the patient or person having a wound that is being treated by application and operation of the device 10. The wound treatment device 10 further includes an attachment surface generally held in a plane or surface that is coincident with the plane or surface of the person's skin. Together these two surfaces define an enclosed, non-contact volume over a wound treatment site.

The wound treatment device 10 that is illustrated in FIG. 1 may be considered in a general way for the purpose of description. In this regard, the description of a wound treatment device is aided by considering three separate parts of the wound treatment device 10. These parts are an attachment portion 12, a wound treatment portion 14, and a transition portion 16. Each portion is designed to serve a separate function.

The attachment portion 12 is used to connect the wound treatment device 10 to the skin of a patient. The wound treatment portion 14 of the wound treatment device 10 defines a vertical extent or dimension of the wound treatment device 10, and thus defines the location of the attachment surface. The transition portion 16 connects the attachment portion 12 to the wound treatment portion 14. The transition portion 16 is provided to improve the comfort and utility of the wound treatment device 10 when the patient moves and stretches the device.

FIG. 1 is a perspective view of a wound treatment device 10 applied to a patient's skin surface 18. A coordinate system 11 is depicted on the patient's skin surface 18 and it defines X, Y and Z directions. An attachment portion 12 is formed as an planar rim or flange. This attachment portion 12 is attached to the patient's skin 18 with an adhesive and it lies in a first XY plane. In this embodiment of wound treatment device 10, a transition portion 16 is integrally formed with attachment portion 12. Transition portion 16 rises from the skin surface in the Z direction to connect to a wound treatment portion 14. In this embodiment, wound treatment portion 14 has a transparent planar wound cover 20 which allows one to see a wound treatment area 28. Wound cover 20 is supported above the first XY plane by a foam ring standoff 15. Wound cover 20 lies in a second XY plane that is vertically displaced along the Z-axis by foam ring standoff 15 from the first XY plane. Wound cover 20 and foam ring standoff 15 together form wound treatment portion 14. The region over wound treatment area 28 is called a wound treatment volume 24.

In this figure, wound treatment device 10 has been applied to a patient's skin and is in a relaxed state. In this unstressed state one can see an outer periphery 22 of attachment portion 12. An inner periphery 23 is shown by a crease in the structure where it connects to transition portion 16.

Figure 2:
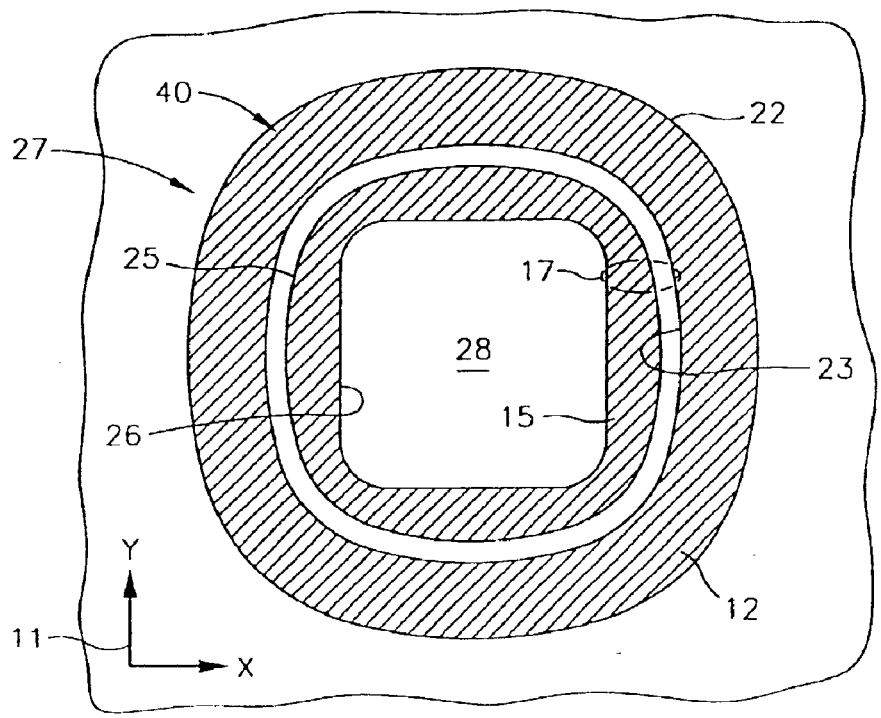
FIG. 2 is a schematic view of projected areas.
Figure 3:
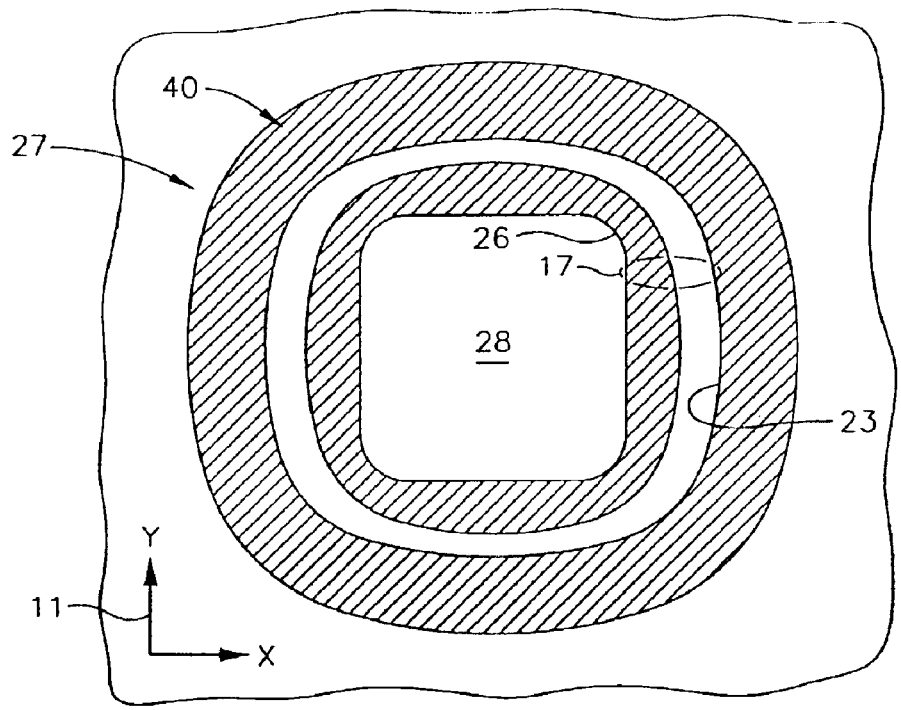
FIG. 3 is a schematic view of projected areas.

FIG. 2 and FIG. 3 should be considered together where they show the influence of patient motion on wound treatment device 10. Both FIG. 2 and FIG. 3 are top views of wound treatment device 10 of FIG. 1 with the various portions of wound treatment device 10 projected onto the first XY plane.

In FIG. 2, the wound covering is shown in a relaxed and un-stretched state having a nominal total projected area 27. Projected wound treatment area 28 is shown at the center of the wound treatment device 10. The outline of foam ring standoff 15 may be seen as the crosshatch area bounded by an exterior perimeter 25 of foam ring standoff 15, and an interior perimeter 26 of foam ring standoff 15. A transition portion projected area 17 is bounded by inner periphery 23 of attachment portion 12; and interior perimeter 26 of foam ring standoff 15. An attachment portion projected area 40 is shown as that cross hatched area bounded by outer periphery 22 and inner periphery 23 of attachment portion 12.

FIG. 3 shows wound treatment device 10 stretched along the X-axis by patient motion. In comparison to FIG. 2, the overall or total projected area 27 of wound treatment device 10 has increased. Attachment portion projected area 40 has increased slightly as attachment portion 12 moves with the underlying skin. Projected wound enclosure area 28 is essentially unchanged in area since in this embodiment foam ring standoff 15 is free move against the skin. The largest percentage area change occurs in transition portion projected area 17. As wound treatment device 10 deforms in response to patient motion, transition portion 16 is compliant and pays out material permitting the majority of the increase in total projected area 27 to be accommodated primarily by transition portion projected area 17.

Figure 4:
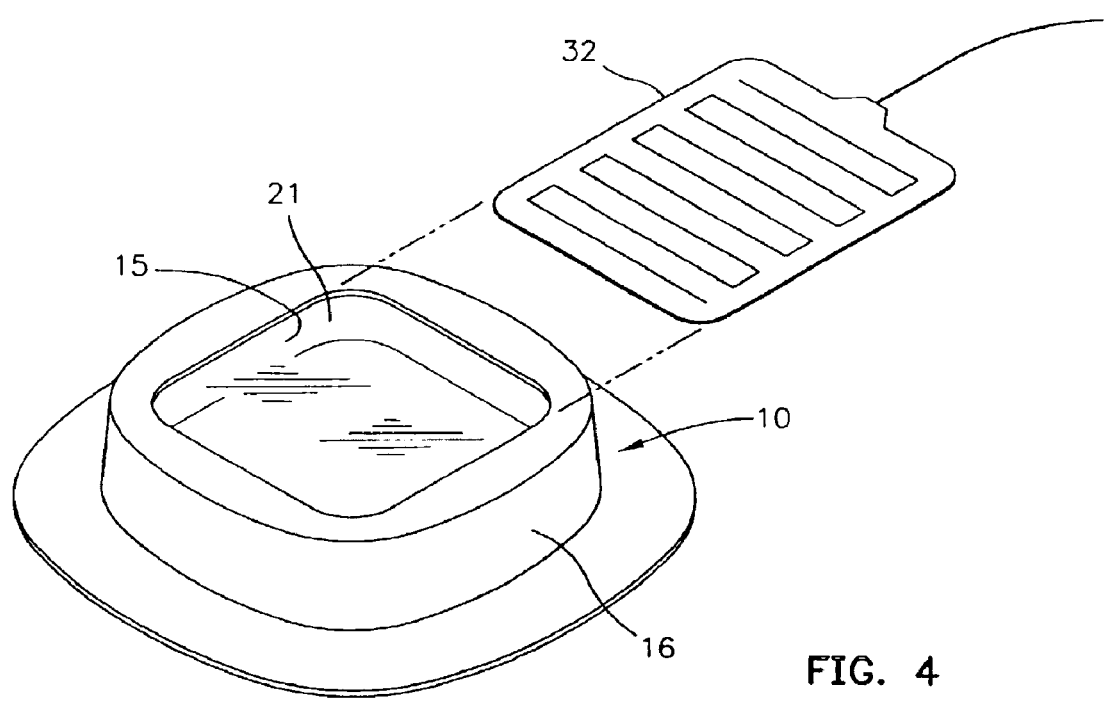
FIG. 4 is a perspective view of a detachable heater in combination with the one embodiment of a wound treatment device.

FIG. 4 shows a detachable heater 32 positioned for insertion into a pocket formed by pocket cover 21. Pocket cover 21 is bonded to wound cover 20 and is sized to retain heater 32. Foam ring standoff 15 and wound cover 20 serve to stabilize the shape of wound treatment device 10 while transition portion 16 accommodates patient motion. Consequently, heater 32 is reliably and comfortably positioned above the wound surface. In general, it is desirable to use a planar heater as heater 32 which has a prescribed heat output per unit area. This form of heater results in a more uniform flux of radiant energy applied to the wound. The amount of heat supplied to the wound area is largely independent of the height of heater 32 above the wound surface within the range of functional heights of this device. In some cases, non-uniform wound area heating might be desirable and therefore the watt density of the heater may be non-uniform across its surface.

Figure 5:
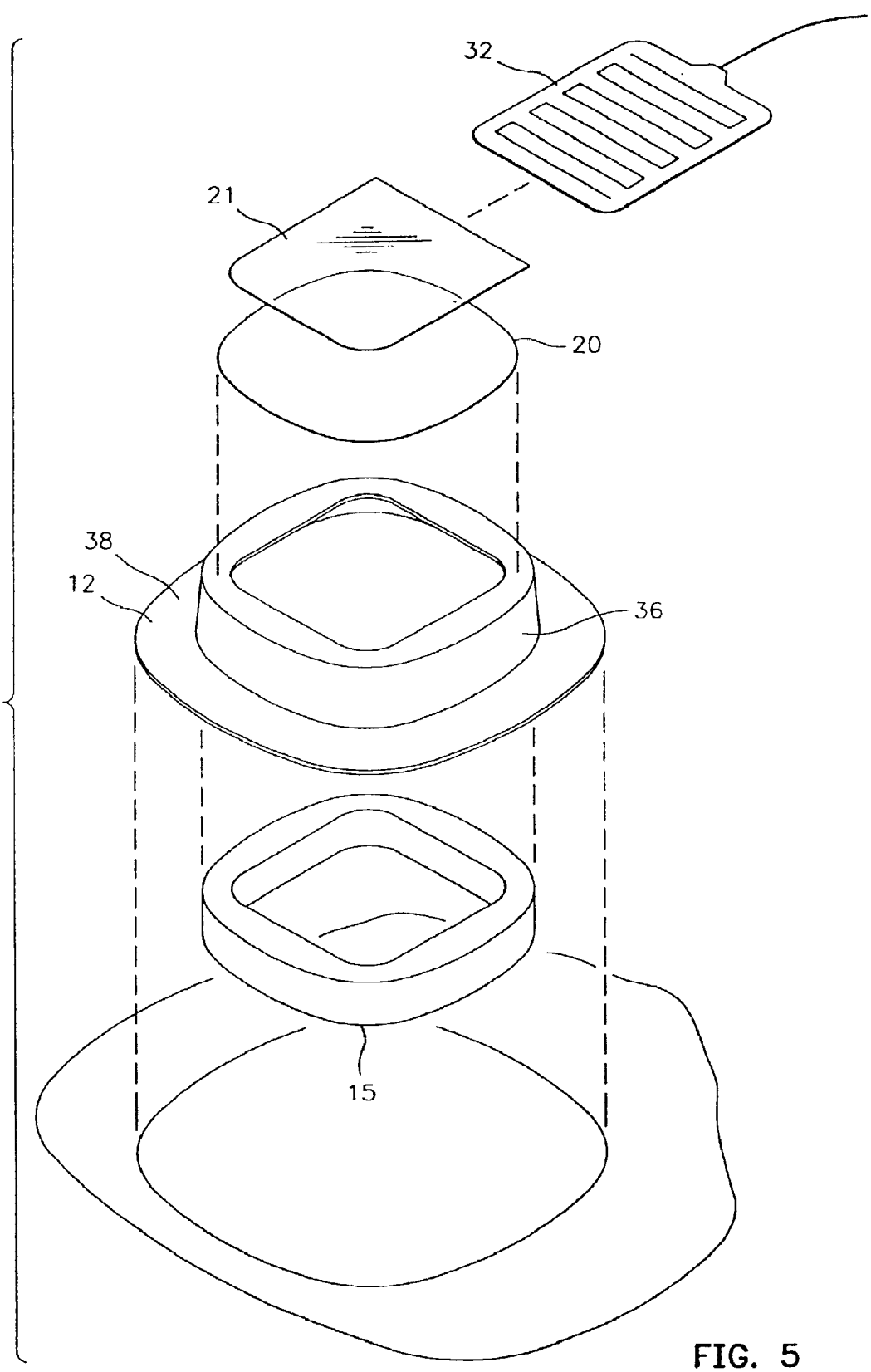
FIG. 5 is an exploded view of the one embodiment of a wound treatment device.

FIG. 5 is an exploded view of the first embodiment of wound treatment device 10. Attachment portion 12 and transition portion membrane 36 are formed as a unitary composite shell 38. Composite shell 38 may be vacuum formed from closed cell polyolefin foams such as Volara-6AS, which is a polyethylene material as sold by Illbruck Inc., of Minneapolis, Minn. It should be apparent that many other materials may be substituted within the scope of the invention. Foam ring standoff 15 may be die cut from foam sheeting of a reticulated polyurethane foam. The absorbency of the foam as well as its mechanical properties can be tailored to the particular wound treatment application. For example, the foam standoff may be impregnated with a medicament such as an antibiotic, antifungal, or antimicrobial material. It may also be desirable to supply a deodorant material or nitric oxide releasing material from the foam standoff. Wound cover 20 and wound pocket 21 may be made from a thin film of polyethylene. In general, the composite shell should be sufficiently self supporting so that when wound treatment device 10 is removed from its release liner, wound treatment portion 14 is held up or supported by the shaped flexion joint of transition portion membrane 36, and some effort is required to evert composite shell 38 and turn it inside out. This behavior defines the self supporting feature which causes foam ring standoff 15 to lie gently against the skin even when wound treatment device 10 is upside down. For larger wound coverings it may be desirable to apply a tacky adhesive to the patient contact surface of the standoff.

Figure 6:
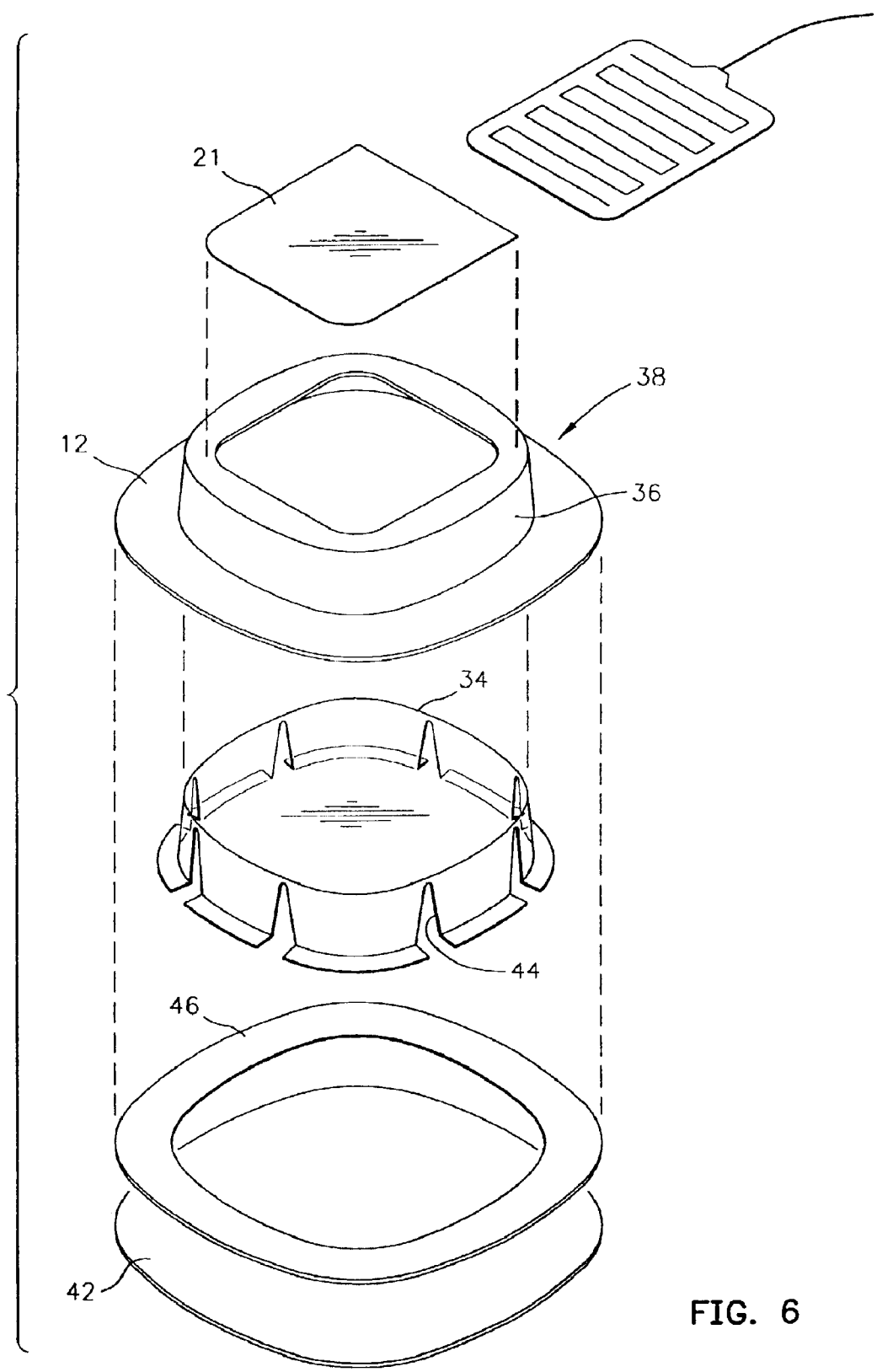
FIG. 6 is an exploded view of another embodiment of a wound treatment device.

FIG. 6 is an exploded view of another embodiment of wound treatment device 10. Attachment portion 12 and transition portion membrane 36 are formed as a unitary composite shell 38. In this embodiment, the wound treatment volume is defined by a serrated cup standoff 34. Standoff 34 may be made from a more rigid polymeric material, such as polyethylene, or the like. The serrations typified by a plurality of serrations 44 permit serrated cup standoff 34 to flex and accommodate patient motion. This embodiment shows a release liner 42 coupled to attachment portion 12 of composite shell 38 with an adhesive 46. In this embodiment, pocket cover 21 is bonded to composite shell 38.

Figure 7:
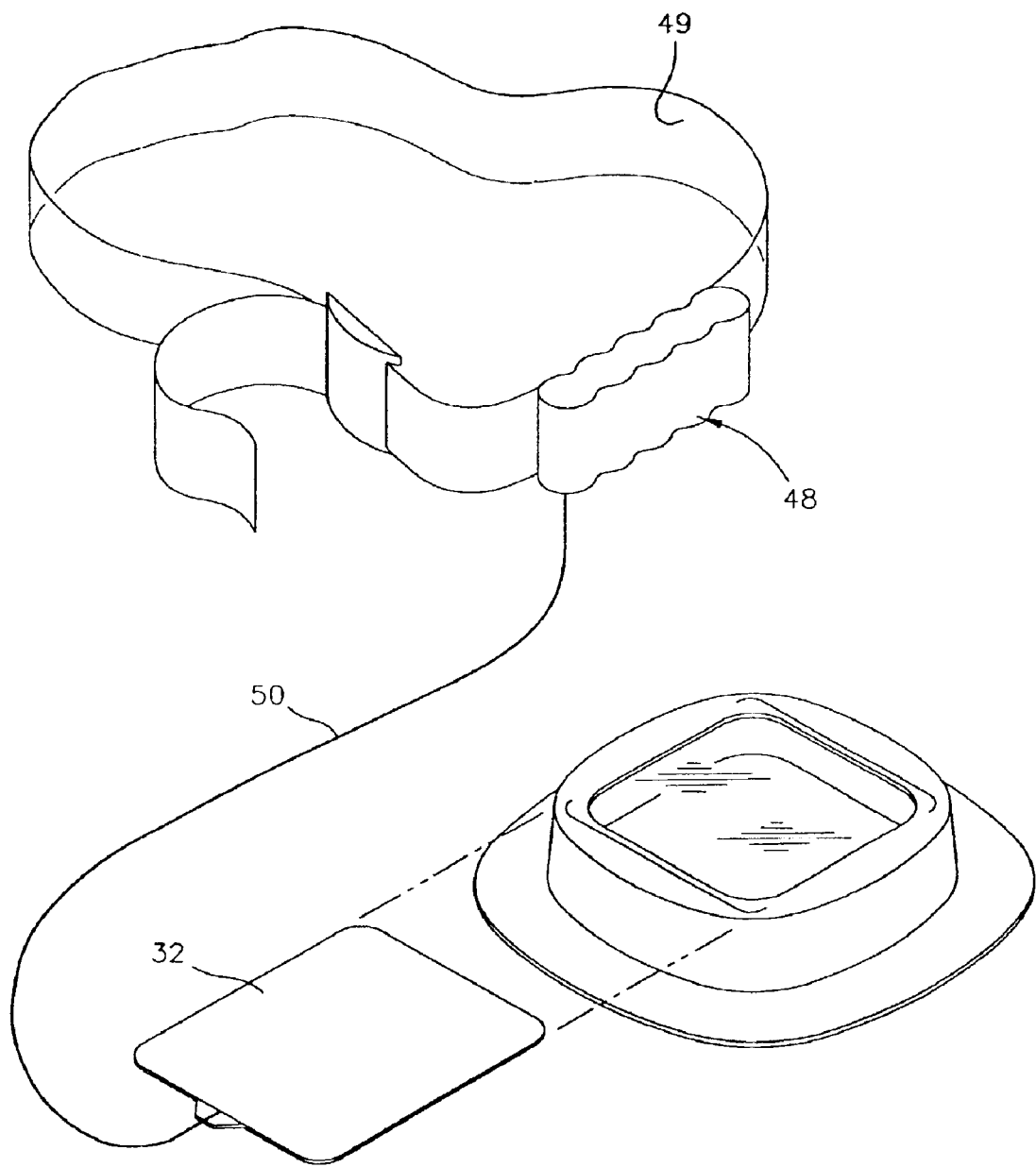
FIG. 7 is a perspective view of a heater system.

FIG. 7 depicts a portable power supply 48 to provide for the ambulatory use of the heated versions of the wound treatment device. A collection of battery cells may be wired together to form power supply 48 which may be conveniently attached to a belt 49. A suitable cable 50 may be used to conduct power to heater 32. In many instances, it may be desirable to cut off power to heater 32 if wound treatment device 10 is collapsed against the wound so as to prevent overheating of the wound surface.

FIG. 8 shows a schematic representation of a touch switch 52 which may be incorporated directly into detachable heater 32. Heater 32 includes a continuous resistive heating coil 51. A conductive membrane makes up touch switch 52 and is arranged near heating coil 51 so that it may "short out" segments or portions of coil 51 it touches. In use, all power to heating coil 51 is completely turned off by pressure applied to an entire touch sensor 53.

FIG. 9A shows an exploded version of heater 32 incorporating a touch switch 52 of the type described schematically in FIG. 8. A switch cover 45 has a conductive membrane which is located over the conductive pattern of heating coil 51. It is held in position with an adhesive band 54. FIG. 9B shows the underside of switch cover 45 showing a plurality of discrete insulation bumps typified by a bump 47 which serve to space and support touch switch 52 above heating coil pattern 51. Pressure supplied to switch cover 45 inactivates heater coil 51.

FIG. 10 shows an accessory device 55 or cover. This may take the form of a passive heater (or insulator) with a reflective surface facing the wound. Accessory device 55 may also take the form of a mapping grid where a grid work of lines is positioned on a transparent card to permit tracking of the wound healing process.

FIG. 11A through FIG. 11D should be considered together. These drawings facilitate a description of the connection of the various structures of the invention and represent several alternative connection geometries. In general, to accommodate patient motion, the transition portion pays out stored material to increase the projected area of the transition portion. Each of these drawings represents a mechanical schematic cross section of a wound treatment device 10 in the XZ plane. In each Figure, the wound covering is in the relaxed state.

Figure 11A:
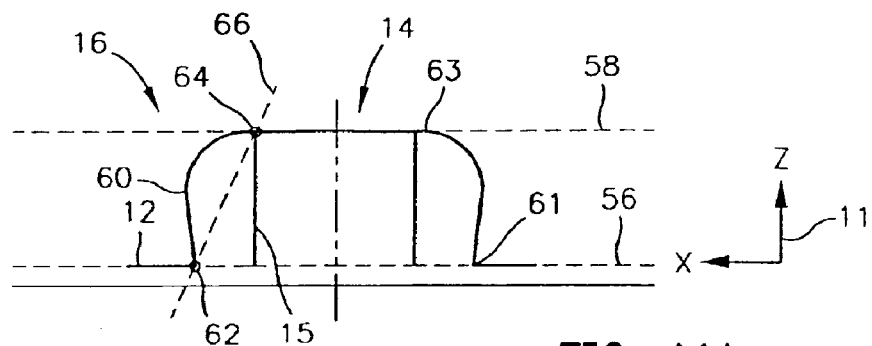
FIG. 11A is a schematic drawing depicting an alternate geometry for the transition portion.

FIG. 11A shows a schematic view of a ring standoff 15 extending from a first plane 56 to a second plane 58. Transition portion 16 has a transition portion membrane 60 which is coupled to attachment portion 12 by a first flexible connection 62 formed at the intersection of attachment portion 12 and transition portion 16. Transition portion membrane 60 is connected to treatment portion 14 at a second flexible connection 64 which is formed at the intersection of transition portion 16 and wound treatment portion 14. Wound treatment portion 14 is generally a cylindrical cup-shaped structure defining a wound treatment area on the patient skin surface. A minimum interconnection distance 66 is depicted as a dashed line extending from first flexible connection 62 to second flexible connection 64. The length of minimum interconnection distance 66 can be used to characterize the "length" of transition portion membrane 60. For many embodiments of the invention, the length of transition portion 16 between first flexible connection 62 and second flexible connection 64 is greater than the length of the straight line drawn between these points. This relationship is true for many embodiments of the wound treatment device when they are in the relaxed or unstressed position. It should be noted that the vertical distance between first plane 56 and second plane 58 represents a minimum value for minimum interconnection distance 66. In the XY plane, first flexible connection 62 forms a first perimeter 61 and a second perimeter 63. In the embodiment depicted in FIG. 11A, first perimeter 61 is larger than second perimeter 63.

Figure 11B:
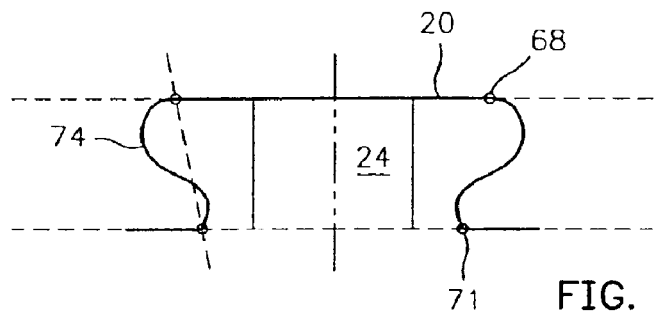
FIG. 11B is a schematic drawing depicting an alternate geometry for the transition portion.

FIG. 11B is a mechanical schematic diagram which represents a cross section of another embodiment of the wound treatment device 10 with an alternate connection geometry. In this drawing, wound cover 20 extends radially beyond wound treatment volume 24 so that a second perimeter 68 is greater than a first perimeter 71. This generates a reflex transition portion 74 construction which may be adopted to increase the "length" and amount of material in the reflex transition portion 74.

Figure 11C:
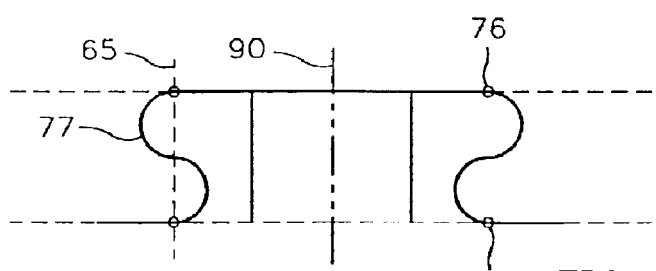
FIG. 11C is a schematic drawing depicting an alternate geometry for the transition portion.

FIG. 11C shows a construction where a first perimeter 76 and a second perimeter 78 have approximately the same value and are both concentric with an axis 90. This construction can produce an undulated transition portion 77. Once again, the length of undulated transition portion 77 exceeds the length of a line 65 between first perimeter 76 and second perimeter 78.

Figure 11D:
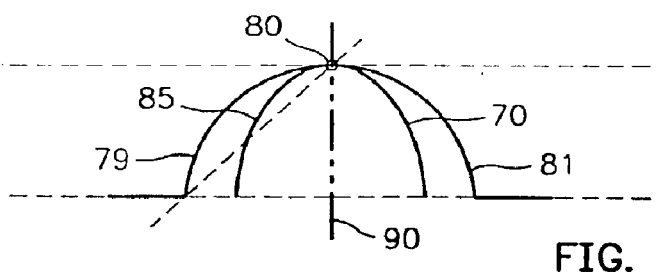
FIG. 11D is a schematic drawing depicting an alternate geometry for the transition portion.

FIG. 11D shows a hemispheric shell 70 as wound treatment portion 14. In this embodiment a second perimeter 80 is a single line of attachment that is generally concentric with axis 90. In this embodiment, a first perimeter 81 has a length which greatly exceeds the length of second perimeter 80. This construction forms a hemispheric transition portion 79 which has a length which exceeds the linear distance between second perimeter 80 and first perimeter 81 along a line 85.

Although the various geometries vary in detail, it is preferable to form transition portion 16 from a resilient material which is generally self-supporting, yet sufficiently flexible so that it acts as a compliant hinge mechanism. This flexibility substantially limits the transfer of shearing force from wound treatment portion 14 to attachment portion 12 of the wound treatment device 10, and visa versa. With the geometries set forth in FIG. 11A through FIG. 11D, transition portion 16 of wound treatment device 10 forms a shaped flexion joint or formed expansion joint which stores "material" in a pleat, convolution, bellows, or the like. This type of structure provides a means for expanding the size of transition portion 16 resulting in minimizing the transfer of forces from attachment portion 12 to wound treatment portion 14.

FIG. 12A through FIG. 14B should be considered together. In these embodiments of the invention, the standoff structure reduces in height resulting in increased transition portion projected area 17 during the stretching of the wound treatment device.

Figure 12A:
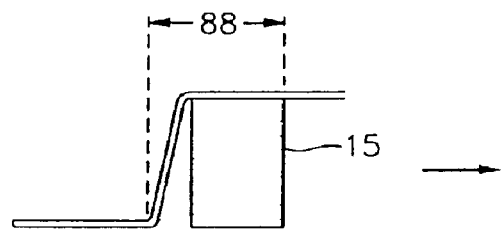
FIG. 12A is a schematic drawing depicting functional relationships between several elements of the invention.
Figure 12B:
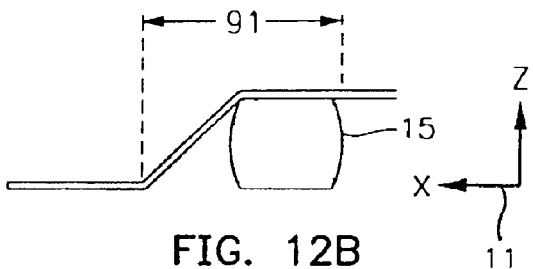
FIG. 12B is a schematic drawing depicting functional relationships between several elements of the invention.

FIG. 12A shows a part of a wound treatment device having foam ring standoff 15 in the unstressed or relaxed state. In this instance, transition portion projected area 17 is proportional to a dimension 88. In FIG. 12B, the wound treatment device has been stretched and the height of foam ring standoff 15 is reduced in the Z direction which has increased transition portion projected area 17 as represented by dimension 91.

Figure 13A:
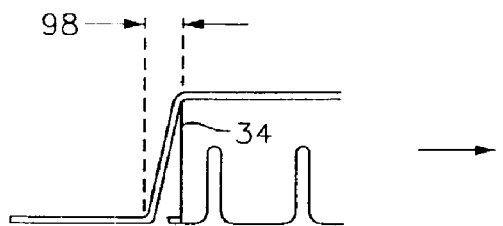
FIG. 13A is a schematic drawing depicting functional relationships between several elements of the invention.
Figure 13B:
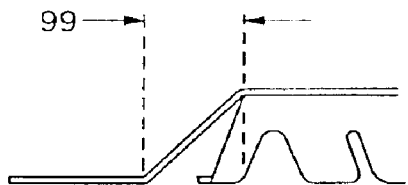
FIG. 13B is a schematic drawing depicting functional relationships between several elements of the invention.

FIG. 13A shows a part of a wound treatment device having serrated cup standoff 34 in the unstressed or relaxed state. In this instance, transition portion projected area 17 is proportional to a dimension 98. In FIG. 13B, the wound treatment device has been stretched, and the height of serrated cup standoff 34 is reduced in the Z direction. The serrated wall sections splay out to permit the height reduction which increases transition portion projected area 17 as represented by a dimension 99.

Figure 14A:
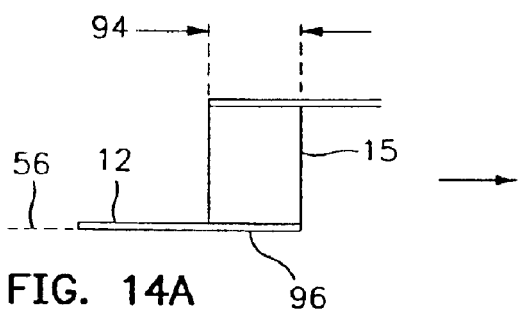
FIG. 14A is a schematic drawing depicting functional relationships between several elements of the invention.
Figure 14B:
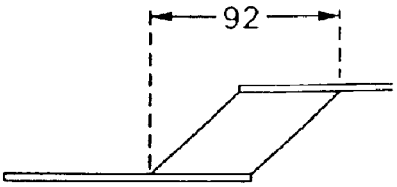
FIG. 14B is a schematic drawing depicting functional relationships between several elements of the invention.

FIG. 14A shows a part of a wound treatment device having foam ring standoff 15 in the unstressed or relaxed state. However, in this construction attachment portion 12 and a transition portion membrane 96 lie entirely in first plane 56. In this instance, transition portion projected area 17 is proportional to a dimension 94. In FIG. 14B, the wound treatment device has been stretched and the height of the foam ring standoff 15 is reduced in the Z direction. This height reduction increases transition portion projected area 17 represented by a dimension 92.

The Invention

Our flexible, non-contact wound treatment device is illustrated in FIGS. 15–19B where the same reference numerals specify identical parts throughout the drawings.

Figure 15:
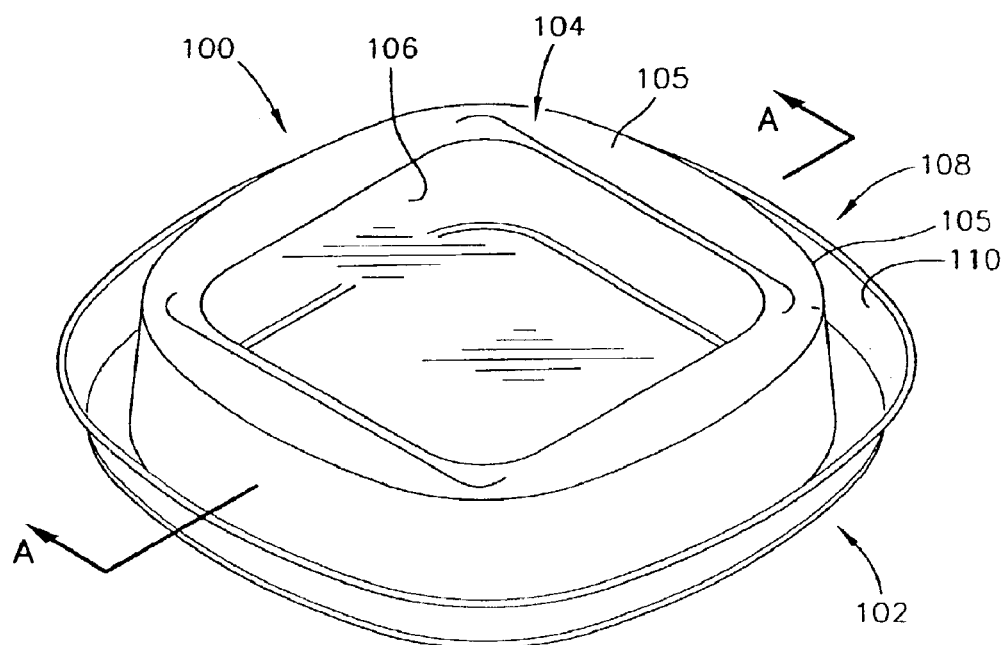
FIG. 15 is a perspective view of the preferred embodiment of a flexible non-contact wound treatment device that embodies our invention.

FIG. 15 is a perspective view of a flexible, non-contact wound treatment device 100 for application to a patient's skin surface. An attachment portion 102 is formed as a collar or flange. This attachment portion 102 is for attachment around a wound through an adhesive layer on the underside of the attachment portion. Our preferred embodiment of wound treatment device 100 also embraces a wound treatment portion 104 that includes a wound cover 105, described below, supported by a support member in the form of a standoff 106. A transition portion 108 connects the wound treatment portion 104 to the attachment portion 102 and preferably includes a membrane 110 that extends around an outer periphery of the support member 106 and is attached to the attachment portion 102 between inner and outer peripheries thereof.

Figure 17:
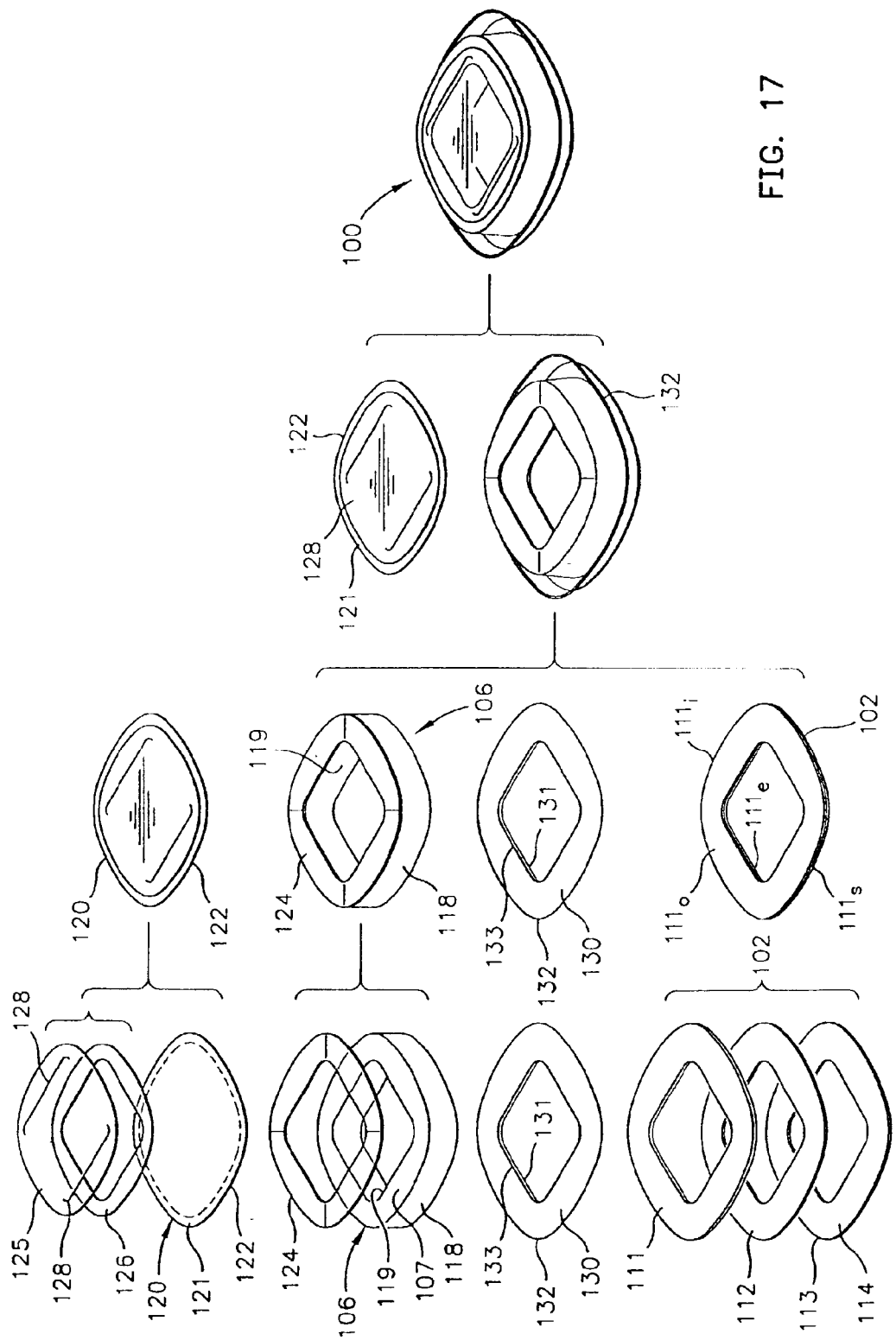
FIG. 17 is an exploded view of our preferred embodiment.

Referring now to FIGS. 15 and 17, in the wound treatment device 100, the attachment portion 102 is an integrated, unitary assembly preferably having three sections: a foam layer 111, an adhesive film layer 112 on a bottom surface of the foam layer 111, and a release liner 113 covering the adhesive film layer 112. One or more lines of weakness or perforation 114 are provided on the release liner 113 so that its parts may be separated and selectably peeled off of the adhesive film layer 112, thereby to expose the adhesive film layer 112 a section at a time for application to a person's skin. The foam layer 111 may comprise a naturally open-celled polyurethane foam. The foam layer 111 is preferably approximately ⅛" thick. The adhesive film layer 112 may comprise a high MVTR thin film, pressure sensitive adhesive (PSA) laminate available as a package under the trade name Mediderm from Bertek. The foam layer 111 is heat bonded to the adhesive film layer 112. The material of which the adhesive film layer 112 is comprised is selected for a combination of adhesion level, permeability, and conformability (stretching and flexing with the skin) to allow prolonged skin contact, without complications. The release liner 113 is a white release paper coated with a release agent that is provided on the Mediderm 3701 product. The perforations or slits 114 are made during assembly to aid in the removal of the release liner 113 prior to attachment of a wound treatment device to a person.

When 111, 112 and 113 are assembled, the attachment portion 102 is a flexible collar shaped part with an inner periphery portion 111$i$ on an upper surface 111$s$ of the foam layer 111 around an inner perimeter, or edge, 111$e$. The upper surface 111$s$ faces, and is therefore disposed under, or beneath, the support member 106. The attachment portion 102 further includes an outer perimeter, or edge, 111$o$.

The wound treatment portion 104 includes the support member 106, which is preferably a ring of absorbent foam such as a naturally open-celled polyurethane foam that is selected to have favorable characteristics of absorbency, leaking and resevoiring. Such material is available as a product sold under the trade name Aquazone from Foamex. The support member 106 has an upper surface 107, a lower surface (109 in FIGS. 18B–19B), an outer perimeter, or edge, 118 and an inner perimeter, or edge, 119. The thickness of the support member 106 is preferably in a range extending from ½" to ⅝", with the exact dimension being selected to maintain non-contact at wound sites whereby, during use, the foam ring can compress and conform without the wound cover contacting the wound. The wound cover 105 in the preferred embodiment includes a layer 120 preferably of 4 mil.-thick clear, flexible polyurethane film with favorable characteristics selected, but not limited, to include moisture vapor transfer, oxygen permeability, and transmission of infrared radiation. Such material is available as a product sold under the trade name Deerfield 6100S. The layer 120 is attached to the upper surface 107 of the support member 106 by a ring 124 of adhesive comprising a synthetic rubber-base adhesive such the product sold under the trade name HL-2306-X by H. B. Fuller Adhesive. When the layer 120 is attached to the upper surface 107 of the support member 106, a perimeter portion 121 of the layer 120 extends out beyond the outer perimeter 118 of the support member 106. The wound cover 105 further includes a stretcher layer 125 attached to the layer 120 so that the layer 120 is sandwiched between the stretcher layer 125 and the upper surface 107 of the support member 106. The stretcher layer 125 is a 5 mil-thick planar sheet of (preferably) clear, somewhat flexible polyester film having enough stiffness to aid in maintaining planarity of the wound treatment portion 104. The function of the stretcher layer 125 is to hold the layer 120 taut, much as a "stretcher frame" tautens an artist's canvas.

The stretcher layer 125 is attached to the layer 120 by a layer 126 of adhesive comprising a clear flexible polyester carrier film coated on both sides with an aggressive adhesive. The adhesive layer 126 is oriented over the support member 106. A film carrier allows for the adhesive to be run in a web process and die cut during manufacturing of the stretcher layer 125. The stretcher layer 125 further includes a pair of slits 128 that receive a detachable heater. With the provision of the slits 128, a pocket is formed between the stretcher layer 125 and the layer 120.

The transition portion 108 includes a lower collar 130 that is preferably formed from the same material as the layer 120. The transition portion 108 also includes the outer perimeter portion 121 of the layer 120 that extends out beyond the support member 106 when assembled thereto. When the wound treatment device 100 is assembled, a circumferential edge 122 of the layer 120 is joined to a corresponding circumferential edge 132 of the lower collar 130. Preferably, the edges 122 and 132 are sealed or welded together by a heat process. When so joined, the outer perimeter portion 121 of the layer 120 and the lower collar 130 form the membrane 110, which extends over the outside of the outer perimeter 118 of the support member 106. The lower collar has a ring-like shape that includes an inner periphery 131. An inner periphery portion 133 comprises an annular portion of the lower collar material on a surface of the lower collar that faces away from the lower surface 109 of the support member 106. The lower surface 109 is not shown in FIG. 17, but may be seen in FIGS. 19A and 19B.

The membrane 110 of the transition portion 108 is attached to the attachment portion 102 by heat-bonding or otherwise connecting the inner periphery portion 133 of the lower collar 130 at or near the opposing inner periphery portion 111$i$ of the attachment portion 102.

Many variations of the assembly illustrated in FIGS. 15 and 17 are possible. For example, the support member 106 could be contained within the structure formed by the layer 120, lower collar 130, and attachment portion 102, unattached to any portion of the structure.

Figure 16:
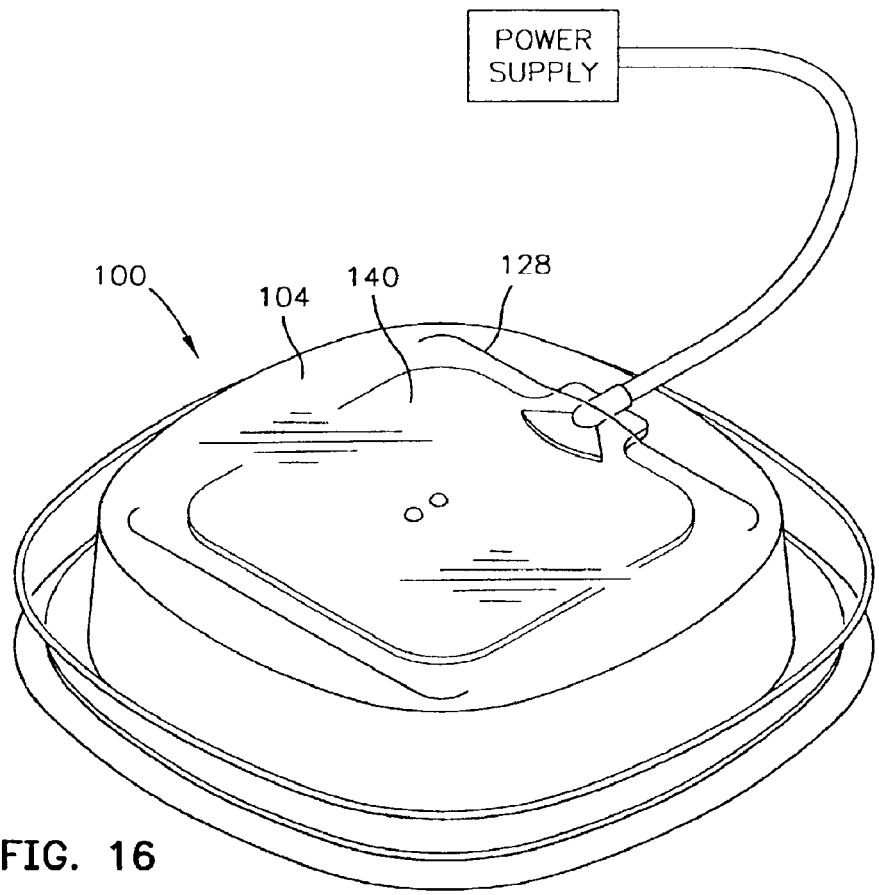
FIG. 16 is a perspective view of a detachable heater in combination with our preferred embodiment.

FIG. 16 shows a detachable heater 140 positioned on the wound cover 105 within a pocket formed between the layer 120 and the stretcher layer 125, with the opening to the pocket provided by one of the slits 128. The wound cover 105, with the heater 140 contained within the pocket, is supported substantially in a plane or surface above a wound by the support member 106. The heater 140 is generally planar and may be connected to and powered by a portable power supply such as that illustrated in FIG. 7.

Figure 18A:
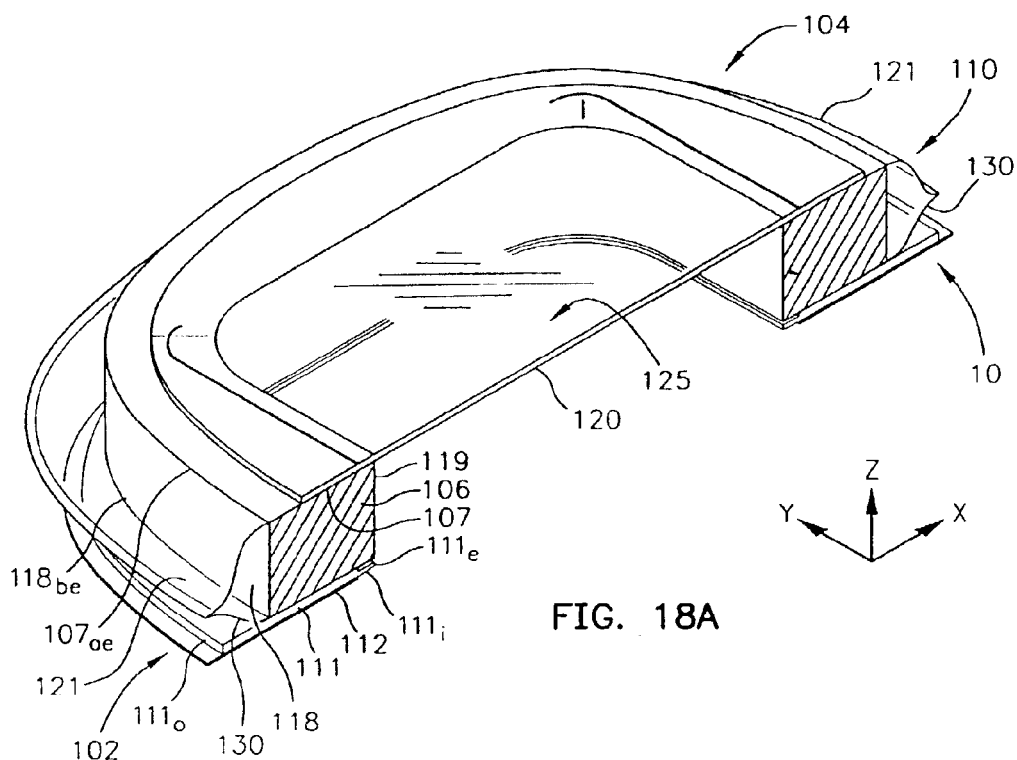
FIG. 18A is a cross-sectional perspective view of our preferred embodiment of the present invention.
Figure 18B:
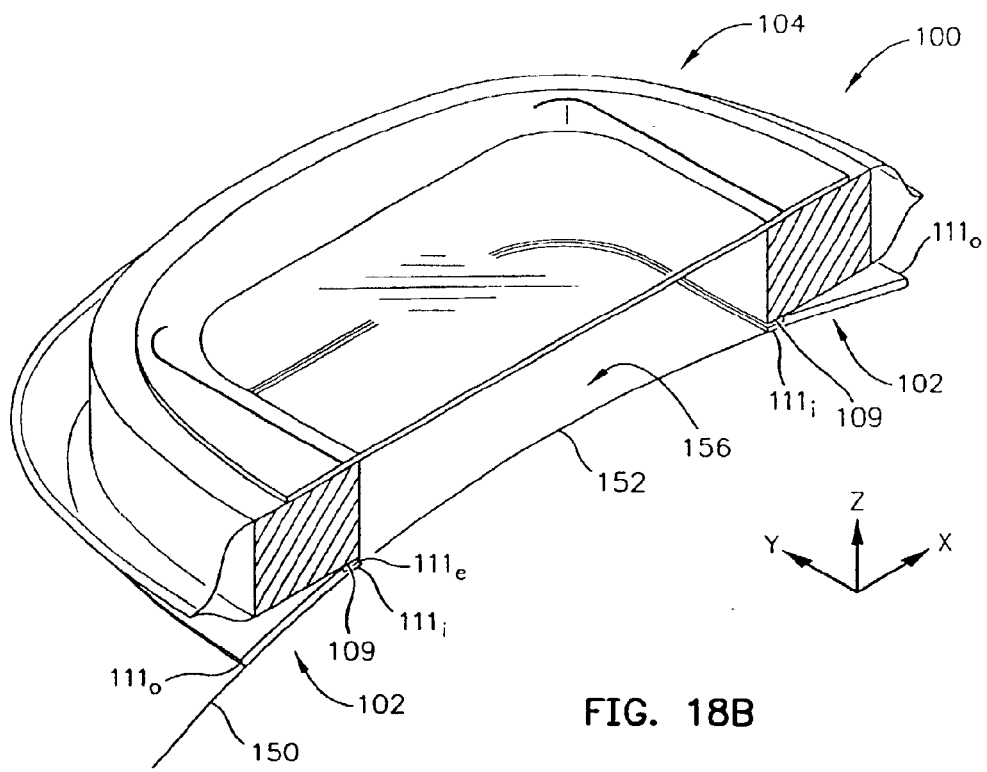
FIG. 18B is the cross-sectional perspective view of our preferred embodiment showing the operation of a membrane in adapting the wound treatment device to body motion.
Figure 18C:
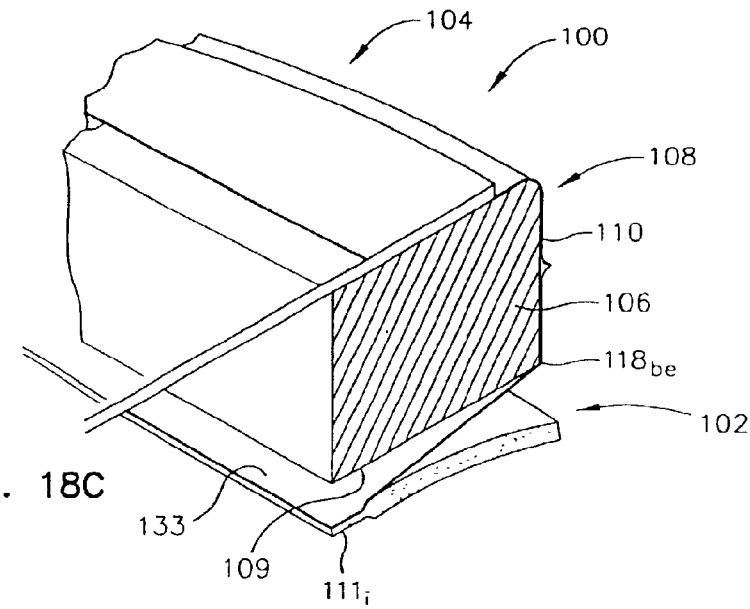
FIG. 18C is a magnified partial cross-sectional view of our preferred embodiment showing further operation of the membrane in accommodating body motion.

Refer now to FIGS. 18A–18C in which FIGS. 18A and 18B show details of the wound treatment device 100 when assembled and put in use. FIG. 18A illustrates the relationship of the attachment portion 102 with respect to the support member 106 of the wound treatment portion 104. In this regard, when the wound treatment device is assembled and placed on a flat surface, the attachment portion 102 and wound treatment portion 104 substantially align along the inner perimeters 119 and 111$e$.

The seal between the inner periphery portion 133 of the lower collar 130 and the inner periphery portion 111$i$ of the attachment portion 102 lies beneath the lower surface of the support member 106. This is the surface that is indicated by reference numeral 109 in FIGS. 19A and 19B. Preferably, the seal joining the inner periphery portions 133 and 111$i$ is a continuous, closed-loop seal. Although, for reasons explained below, this is the preferred location of the seal between the lower collar 130 and attachment portion 102, the inventors contemplate that the seal could comprise a substantially continuous, closed-loop trace anywhere between the outer perimeter 111o and inner perimeter 111e of the attachment member 102.

In FIGS. 17 and 18A, the seal between the edges 122 and 132 of the layer 120 and lower collar 130 is exaggerated as a flange. In practice, the shape of the membrane 110 extending from an upper outer edge 107ue of the upper surface 107 to a lower outer edge 118be of the outer perimeter 118 is rather elongated, with the flange much less pronounced than shown in FIG. 18A. Of course, the membrane 110 in the extent from the edge 107ue all the way down to the seal that joins the inner periphery portions 133 and 111i is not attached, and is therefore free from, although in close proximity to, the outer perimeter 118, lower edge 118be and lower surface 109 of the support member 106.

Figure 19A:
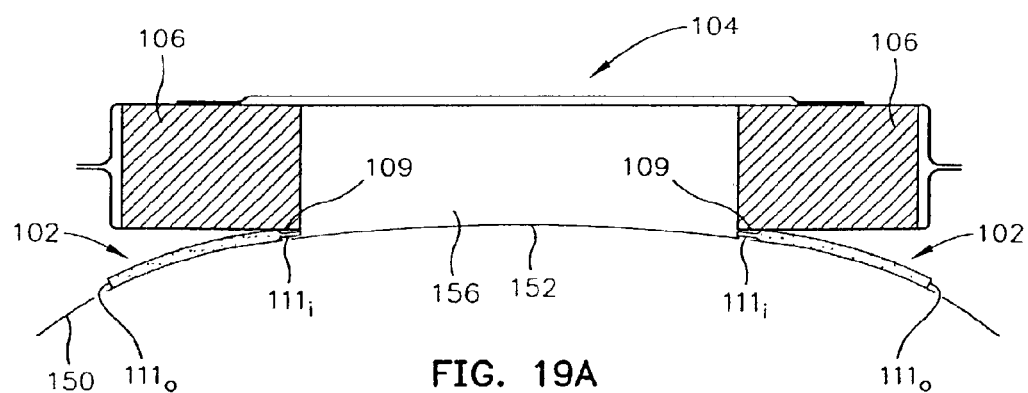
FIG. 19A is a side elevational view of the cross-sectional view of FIG. 18B when attached to a human patient.
Figure 19B:
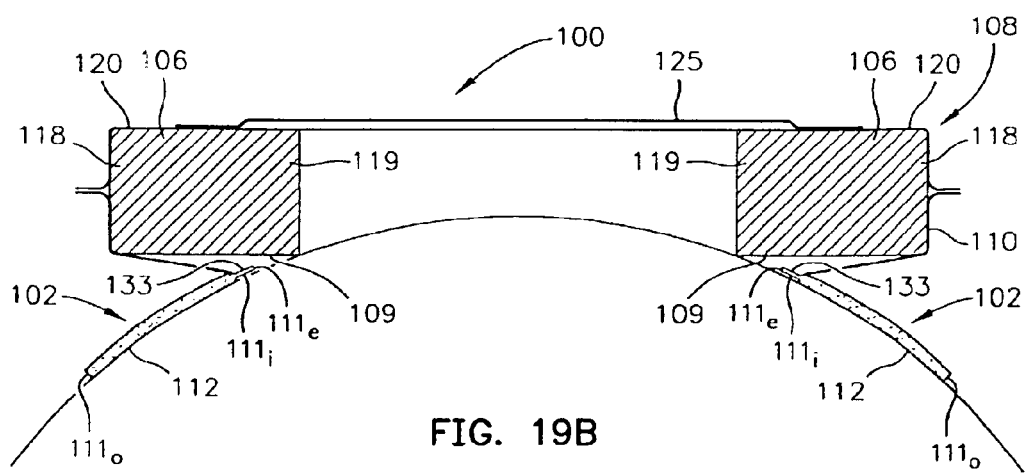
FIG. 19B is a side elevational view representing the cross-sectional view of FIG. 18C.

Referring now to FIGS. 18B–19B, the flexible, non-contact wound treatment device 100 of this invention is suitable for placement onto a skin surface 150 of a patient or person so as to include a selected wound area 152 that abuts a treatment volume 156 within the wound treatment device 100. This attachment may be directly to the skin surface 150, or on another member such as an ostomy ring that is, in turn, mounted or attached to the skin surface 150. As FIGS. 18B–19B demonstrate, the flexible, non-contact wound treatment device 100 of this invention satisfies the objective previously stated by a capability of being conformably attached to an uneven, changing surface supporting a wound treatment portion 104 that remains reasonably or substantially planar in its shape, regardless of body contour or movements. In this regard, as FIGS. 18B and 19B illustrate, the attachment portion 102 operates as a hinge or flexion joint that pivots at the seal between the inner periphery portions 133 and 111i. Relatedly, the attachment portion 102 is free to conform to the shape of the skin surface by flexibly deforming between the inner and outer perimeters 111e and 111o. At the same time, the wound treatment portion 104 is relatively undeformed so that the support member 106 is able to support the layer 120 and stretcher layer 125 in a relatively planar orientation with respect to the wound area 152. In the meantime, the wound treatment device 100 forms a barrier between the wound treatment volume 156 and the ambient atmosphere by virtue of the seal between the edges 122 and 132 of the layer 120 and lower collar 130, and the seal between the inner periphery portions 133 and 111i. The bottom of the wound treatment device 100 is sealed to the skin 150 when the release layer 113 is peeled off so that the adhesive film layer 112 seals to the skin surface 150.

FIGS. 18C and 19B illustrate the conformability of the wound treatment device 100 provided by flexion of the membrane 110 in the transition portion 108. FIGS. 18C and 19B are "snap shots" of the flexible, non-contact wound treatment device 100 after placement as described above with reference to FIGS. 18B and 19A and after movement of a body part on which the device 100 is placed. In these figures, movement is accommodated by excess length in the membrane 110. In FIGS. 18C and 19B, the membrane 110 has tensioned along the perimeter 118 to provide strain relief between the lower edge 118be of the support member 106 and the seal between the inner periphery portions 133 and 111i. In addition, the flexibility of the membrane 110 and its freedom from the outer perimeter 118 and lower surface 109 permit a play out of excess length of the membrane 110 that abuts the outer perimeter 118 of the support member 106. This moves the membrane 110 into close touching engagement with the outer perimeter 118, while lengthening the amount of membrane 110 available between the lower edge 118be and the inner periphery portion 111i.

In another aspect, as FIGS. 18C and 19B show, the membrane 110 acts as a double hinge or a double pleat between the lower edge 118be of the support member 106 and the attachment portion 102. A first hinge pivot or pleat is at the seal between 133 and 111i. This hinge permits the attachment portion to pivot toward and away from the wound treatment portion. The second hinge—at edge 118be—allows the wound treatment portion to move toward and away from the attachment portion. Manifestly, the same effect could be achieved by attachment of the membrane 110 to the lower surface 109 inside of the edge 118be.

Three significant advantages result from placement of the attachment portion 102 beneath the support member 106 of the wound treatment portion.

First, in plan, the shapes and extents of the bottom surface 109 and the attachment portion 102 align and largely overlap, thereby reducing the "foot print" of the wound treatment device 100 to a single, substantially annular shape from the two concentric shapes of FIGS. 2 and 3.

Next, the double hinge (or pleat) provided by the membrane 110 increases the conformability of the wound treatment device to shape and movement, while maintaining the planarity of the wound cover and preventing its contact with a wound.

Last, the lower collar 130, in extending substantially to the inner perimeter 111e of the attachment portion 102 forms a barrier to moisture and wound exudate which may be absorbed by the support member 106, thereby reducing maceration of skin underneath the attachment portion 102.

While the invention has been illustrated by means of specific embodiments and examples of use, it will be evident to those skilled in the art that many variations and modifications may be made therein without deviating from the scope and spirit of the invention. However, it is to be understood that the scope of the present invention is to be limited only by the appended claims.

What is claimed is:

1. A non-contact wound treatment device, comprising:
   a flexible attachment portion including an outer perimeter and an inner perimeter surrounded by the outer perimeter;
   a wound cover including a layer of flexible material with a peripheral portion;
   a transition portion including a membrane connecting the wound cover to the attachment portion, the membrane acting between the peripheral portion and the attachment portion and attached to the attachment portion between the inner and outer perimeters of the attachment portion;
   the attachment portion, the wound cover and the membrane forming a structure; and
   a support member disposed in the structure, over the attachment portion, unattached to the structure.

2. The non-contact wound treatment device of claim 1 wherein the support member has an outer perimeter and the membrane extends around the outer perimeter of the support member.

3. The non-contact wound treatment device of claim 2 wherein the layer of flexible material extends around the outer perimeter of the support member and attaches to the membrane proximate the outer perimeter enclosing the outer perimeter of the support member.

4. The non-contact wound treatment device of claim 1 wherein the membrane is attached to the attachment portion near the inner perimeter of the attachment portion.

5. The non-contact wound treatment device of claim 4, wherein the support member is a ring that includes an inner perimeter substantially aligned with the inner perimeter of the attachment portion.

6. The non-contact wound treatment device of claim 5, wherein the membrane comprises a collar of flexible material having an outer edge joined to the peripheral portion and an inner perimeter joined to the attachment portion near the inner perimeter of the attachment portion.

7. The non-contact wound treatment device of claim 5, wherein the ring comprises a foam material.

8. The non-contact wound treatment device of claim 7, wherein the foam material is an absorbent foam material.

9. The non-contact wound treatment device of claim 1, wherein the inner perimeter of the attachment portion is surrounded by the outer perimeter of the support member.

10. The non-contact wound treatment device of claim 1, wherein the inner perimeter of the attachment portion is beneath the support member.

11. The non-contact wound treatment device of claim 10, wherein the membrane is attached to the attachment portion near the inner perimeter of the attachment portion.

12. The non-contact wound treatment device of claim 1, the wound cover further including a substantially planar layer of flexible material joined to the layer of flexible material above the upper surface.

13. The non-contact wound treatment device of claim 12 further including a slit in the substantially planar layer, the slit opening into a pocket formed by the substantially planar layer and the layer of flexible material.

14. The non-contact wound treatment device of claim 13 further including a heater disposed in the pocket.

15. The non-contact wound treatment device of claim 14, further including a power supply connected to the heater.

16. The non-contact wound treatment device of claim 1, wherein the attachment portion comprises a layer of foam material.

17. The non-contact wound treatment device of claim 16, wherein the attachment portion further includes adhesive material carried on a surface of the layer of foam material and a release layer carried on the adhesive material.

18. The non-contact wound treatment device of claim 17 wherein the release layer has one or more lines of weakness for permitting a portion of the release layer to be removed from the adhesive material.

19. The non-contact wound treatment device of claim 16, wherein the layer of foam material comprises open-cell foam material.

20. The non-contact wound treatment device of claim 16, wherein the attachment portion has a substantially collar-like shape.

21. The non-contact wound treatment device of claim 1, wherein the wound cover is substantially planar.

22. The non-contact wound treatment device of claim 1, wherein the support member is a ring of absorbent foam material.

23. The non-contact wound treatment device of claim 22, wherein the absorbent foam material is impregnated with a medicament.

24. The non-contact wound treatment device of claim 23, wherein the medicament is selected from the group consisting of an antibiotic material, an antifungal material, an antimicrobrial material, a deodorant material and nitric oxide.

25. A non-contact wound treatment device, comprising:
a flexible attachment portion including an outer perimeter and an inner perimeter surrounded by the outer perimeter;
a wound cover;
a support member with a first surface for supporting the wound cover and a second surface facing the attachment portion; and
a member with at least one hinge acting between the wound cover and the attachment portion and attached to the attachment portion between the outer perimeter and the inner perimeter;
the support member unattached to the attachment portion, the wound cover, and the member.

26. The non-contact wound treatment device of claim 25, wherein the member includes a double hinge having a first pivot near the inner perimeter of the attachment portion and a second pivot near an edge of the second surface.

27. The non-contact wound treatment device of claim 26, wherein the member comprises a membrane.

28. The non-contact wound treatment device of claim 27, wherein the membrane is attached to the attachment member near the inner perimeter.

29. The non-contact wound treatment device of claim 28, wherein the support member is a ring that includes an inner perimeter aligned with the inner perimeter of the attachment member.

30. The non-contact wound treatment device of claim 29, wherein the ring comprises a foam material.

31. The non-contact wound treatment device of claim 27, further including a heater on the wound cover.

32. The non-contact wound treatment device of claim 27 further comprising an outer perimeter of the support member, the outer perimeter is enclosed by the wound cover and the membrane.

33. The non-contact wound treatment device of claim 25, further including a heater on the wound cover.

34. The non-contact wound treatment device of claim 31 or 33, further including a power supply connected to the heater.

35. The non-contact wound treatment device of claim 25 wherein the wound cover is substantially planar.

36. The non-contact wound treatment device of claim 25, wherein the support member is a ring of absorbent foam material that includes an inner perimeter.

37. The non-contact wound treatment device of claim 36, wherein the absorbent foam material is impregnated with a medicament.

38. The non-contact wound treatment device of claim 37, wherein the medicament is selected from the group consisting of an antibiotic material, an antifungal material, an antimicrobrial material, a deodorant material and nitric oxide.

39. A non-contact wound treatment device, comprising:
a flexible attachment portion including an outer perimeter and an inner perimeter surrounded by the outer perimeter;
a wound cover;
a support member with a first surface supporting the wound cover and a second surface facing the attachment portion; and
at least one flexion joint acting between the wound cover and a portion of the attachment member near the inner perimeter;
the support member unattached to the attachment portion, the wound cover, and the flexion joint.

40. The non-contact wound treatment device of claim 39, wherein the at least one flexion joint includes a member having a first pivot near the inner perimeter of the attachment portion and a second pivot near an edge of the second surface.

41. The non-contact wound treatment device of claim 40, wherein the flexion joint comprises a membrane.

42. The non-contact wound treatment device of claim 41, wherein the membrane is attached to the attachment member near the inner perimeter.

43. The non-contact wound treatment device of claim 42, wherein the support member is a ring that includes an inner perimeter aligned with the inner perimeter of the attachment member.

44. The non-contact wound treatment device of claim 43, wherein the ring comprises a foam material.

45. The non-contact wound treatment device of claim 44, further including a substantially planar heater on the wound cover.

46. The non-contact wound treatment device of claim 41 further comprising an outer perimeter of the support member, the outer perimeter is enclosed by the wound cover and the membrane.

47. The non-contact wound treatment device of claim 39, further including a substantially planar heater on the wound cover.

48. The non-contact wound treatment device of claim 39 or 47, further including a power supply connected to the substantially planar heater.

49. The non-contact wound treatment device of claim 39 wherein the wound cover is substantially planar.

50. The non-contact wound treatment device of claim 39, wherein the support member is a ring of absorbent foam material that includes an inner perimeter.

51. The non-contact wound treatment device of claim 50, wherein the absorbent foam material is impregnated with a medicament.

52. The non-contact wound treatment device of claim 51, wherein the medicament is selected from the group consisting of an antibiotic material, an antifungal material, an antimicrobrial material, a deodorant material and nitric oxide.

53. A non-contact wound treatment device, comprising:
a support member with a treatment volume and an outside perimeter;
a cover positioned against the support member, over the treatment volume;
a flexible attachment portion positioned against the support member; and
a transition portion including a membrane connecting the cover to the attachment portion, the membrane extending between the cover and the attachment portion beyond the outside perimeter;
the support member unattached to the cover, the attachment portion, and the transition portion.

54. The non-contact wound treatment device of claim 53, wherein the support member comprises a ring of absorbent foam material with an inner perimeter containing the treatment volume, and the attachment portion is ring-shaped with an inner perimeter.

55. The non-contact wound treatment device of claim 54, wherein the absorbent foam material is impregnated with a medicament.

56. The non-contact wound treatment device of claim 55, wherein the medicament is selected from the group consisting of an antibiotic material, an antifungal material, an antimicrobrial material, a deodorant material and nitric oxide.

57. The non-contact wound treatment device of claim 53, wherein the inner perimeter of the ring is aligned with the inner perimeter of the attachment portion.

58. The non-contact wound treatment device of claim 57, wherein the membrane is attached to the attachment portion near the inner perimeter of the attachment portion.

59. The non-contact wound treatment device of claim 53, wherein the membrane comprises a collar of flexible material having an outer edge joined to a peripheral portion of the cover and an inner perimeter joined to the attachment portion near the inner perimeter of the attachment portion.

60. The non-contact wound treatment device of claim 53, further including a layer of flexible material joined to the cover above the ring.

61. The non-contact wound treatment device of claim 60 further comprising:
a pocket between the layer of flexible material and the cover; and
at least one slit in the layer opening into the pocket.

62. The non-contact wound treatment device of claim 61 further including a heater for being disposed in the pocket.

63. The non-contact wound treatment device of claim 62, further including a power supply for causing the heater to operate.

64. A non-contact treatment device, comprising:
a flexible, absorbent ring with two opposing surfaces;
a cover against a first surface of the ring to form a treatment volume therewith;
a flexible attachment portion against the second surface of the ring; and
a membrane outside of the ring connected to the cover and to the attachment portion;
the ring unattached to the cover, the attachment portion, and the transition portion.

65. The treatment device of claim 64, further comprising a pocket on the cover for receiving a heater.

66. The treatment device of claim 64, further comprising a medicament in the ring.

67. The treatment device of claim 66, further comprising a pocket on the cover for receiving a heater.

68. The treatment device of claim 67, further comprising a heater in the pocket.

69. The treatment device of claim 64, the membrane being connected to the attachment portion to form a hinge therewith.

70. The treatment device of claim 69, further comprising a medicament in the ring.

71. The treatment device of claim 70, further comprising a pocket on the cover for receiving a heater.

* * * * *

UNITED STATES PATENT AND TRADEMARK OFFICE
CERTIFICATE OF CORRECTION

PATENT NO. : 6,987,209 B2
DATED : January 17, 2006
INVENTOR(S) : Augustine et al.

Page 1 of 1

It is certified that error appears in the above-identified patent and that said Letters Patent is hereby corrected as shown below:

<u>Column 16,</u>
Line 47, insert -- The treatment device of claim 71, further comprising a heater in the pocket. --.

Signed and Sealed this

Fourth Day of April, 2006

JON W. DUDAS
*Director of the United States Patent and Trademark Office*

UNITED STATES PATENT AND TRADEMARK OFFICE
CERTIFICATE OF CORRECTION

PATENT NO. : 6,987,209 B2 Page 1 of 1
APPLICATION NO. : 10/291303
DATED : January 17, 2006
INVENTOR(S) : Augustine et al.

It is certified that error appears in the above-identified patent and that said Letters Patent is hereby corrected as shown below:

On the title page item (73), Assignee: should read --Arizant Technologies LLC--.

Signed and Sealed this

Eighth Day of May, 2007

JON W. DUDAS
*Director of the United States Patent and Trademark Office*